(12) United States Patent
Ehringer et al.

(10) Patent No.: US 7,056,529 B2
(45) Date of Patent: *Jun. 6, 2006

(54) DIRECT CELLULAR ENERGY DELIVERY SYSTEM

(75) Inventors: William D. Ehringer, Charlestown, IN (US); Sufan Chien, Floyd Knobbs, IN (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 175 days.

This patent is subject to a terminal disclaimer.

(21) Appl. No.: 10/397,048

(22) Filed: Mar. 25, 2003

(65) Prior Publication Data

US 2003/0235611 A1    Dec. 25, 2003

Related U.S. Application Data

(60) Provisional application No. 60/380,762, filed on May 14, 2002.

(51) Int. Cl.
*A61K 9/127*    (2006.01)

(52) U.S. Cl. .................................... 424/450
(58) Field of Classification Search ................ 424/450
See application file for complete search history.

(56) References Cited

U.S. PATENT DOCUMENTS

| | | | |
|---|---|---|---|
| 5,540,935 A * | 7/1996 | Miyazaki et al. | 424/450 |
| 5,674,528 A | 10/1997 | Ogata et al. | |
| 5,863,556 A * | 1/1999 | Ruckert et al. | 424/450 |
| 6,011,020 A | 1/2000 | Gold et al. | |
| 6,086,851 A | 7/2000 | Boni et al. | |
| 6,399,091 B1 * | 6/2002 | Berthold et al. | 424/443 |
| 6,417,326 B1 * | 7/2002 | Cullis et al. | 530/324 |

FOREIGN PATENT DOCUMENTS

JP    03-236320    10/1991

OTHER PUBLICATIONS

Zang, D.; Daosheng, Z.; Huang, Dingjiu; et al., "The Distribution of Liposome-encapsulated ATP in Experimental ischemic Myocardium," *Chemical Abstracts*, vol. 109, No. 11, Abstract No. B5657M, sep. 12, 1988.

Ainscow, E.K., and Brand, M.D. (1999) Top-down control analysis of ATP turnover, glycolysis and oxidative phosphorylation in rat hepatocytes. Eur. J. Biochem. 263:671-685.

Arakawa A, Isshiguro S, Ohki K, Tamai M. (1998) Preparation of liposome-encapsulating adenosine triphosphate. *Tohuku J Exp Med* 184:39-47.

Brand, M.D. (1995). Measurement of mitochondrial proton motive force. *In* Bioeneergetics, a Pratical Approach / Brown, G.C., and Cooper, C.E., eds. Oxford University Press. Oxford, 39-62.

(Continued)

*Primary Examiner*—Gollamudi S. Kishore
(74) *Attorney, Agent, or Firm*—Jenkins, Wilson, Taylor & Hunt, P.A.

(57) ABSTRACT

A vesicle comprises ATP and a phospholipid which is a stable vesicle former. The vesicle has a fusion rate of at least 20 vesicle fusions/second.

17 Claims, 3 Drawing Sheets

OTHER PUBLICATIONS

Buck, L.T. and P.W. Hochachka, "Anoxic suppression of Na$^+$-K$^+$-ATPase and constant membrane potential in hepatycytes: support for channel arrest," *Am. J. Physiol.* 265 *Regulatory Integrative Comp. Physiol.* 34:R1020-1025 (1993).

Chien, S., "Metabolic Management" *in Organ Procurement and Preservation for Transplantation*, 2$^{nd}$ ed., Ch. 6, pp. 84-109, Springer, Landes Bioscience, Austin, TX (1997).

Connery, C., G. Hicks, and T. Wang, "Positive Correlation of Functional Recovery and Tissue ATP Levels in the Hypothermically Stored Cardiac Explant," *Surgical Forum*, 41:282-284 (1990).

Eckert, D. and P. KIm, "Mechanisms of Viral Membrane Fusion and Its Inhibition," *Annu. Rev. Biochej.*, 70:777-810 (2001).

Ehringer, W., D. Belcher, S. Wassall, and W. Stillwell, "A comparison of the effects of linolenic (18:3Ω3) and docosahexaenoic (22:6Ω3) acids on phospholipid bilayers," *Chem. Phys. Lipids*, 54:79-88 (1990).

Ehringer, W., D. Belcher, S. Wassall, and W. Stillwell, "A comparison of α-linolenic acid (18:3Ω3) and γ-linolenic acid (18:3Ω6) in phosphatidylcholine bilayers," *Chem. Phys. Lipids*, 57:87-96 (1991).

Fedelšová, M., A. Ziegelhöffer, E-G. Krause, and A. Wallenberger, "Effect of Exogenous Adenosine Triphosphate on the Metabolic State of the Excised Hypothermic Dog Heart," *Circulation Res.*, 24:617-627 (1969).

Fraley, R., R. Straubinger, G. Rule, E.L. Springer, and D. Papahadjopoulos, "Liposome-Mediated Delivery of Deoxyribonucleic Acid to Cells: Enhanced Efficiency of Delivery Related to Lipid Composition and Incubation Conditions," *Biochem.*, 20:6978-6987 (1981).

Fremes, S., J. Zhang, R. Furukawa, D. Mickle, et al., "Adenosine Pretreatment for Prolonged Cardiac Storage," *in J. Thorac. Cardiovas. Surg.*, 110(2):293-301 (1995).

Garrett, F., S. Goel, J. Yasul, and R. Koch, "Liposomes fuse with sperm cells and induce activation by delivery of impermeant agents," *Biochem. Et Biophys. Acta*, 1417:77-88 (1999).

Guo-Xing, X., X. Xing-hui, L. Fang-Yu, Z. DeLiang, et al., "Adenosine Triphosphate Liposomes: Encapsulation and Distribution Studies," *Pharmaceut. Res.*, 7(5)553-557 (1990).

Hirasawa, H., K. Soeda, Y, Ohtake, S. Oda, et al., "Effects of ATP-MgCl$_2$ and ATP-Na$_2$ Administration on Renal Function and Cellular Metabolism Following Renal Ischemia," *Circulatory Shock*, 16:337-346 (1985).

Hochachka, P.W. and P.L. Lutz, "Mechanism, origin, and evolution of anoxia tolerance in animals," *Comp. Biochem. Phys.*, Part B, 130:435-459 (2001).

Jahn, R. and T.C. Südhof, "Membrane fusion and exocytosis," *Annu. Rev. Biochem.* 68:863-911.

Katori, M. and R. Berne, "Release of Adenosine from Anoxic Hearts. Relationship to Coronary Flow," *Circulation Res.*, 19:420-425 (1966).

Klein, H., J. Schaper, St. Puschmann, Ch. Nienaber, et al., "Loss of canine myocardial nicotinamide adenine dinucleotides determines the transition from reversible to irreversible ischemic damage of myocardial cells," *Basic Res. Cardiol.*, 76:612-621 (1981).

Kozubek, A., J. Gubernator, E. Przeworska, and M. Stasiuk, "Liposomal drug delivery, a novel approach: PLARosomes," *Acta Biochim. Pol.*, 47(3):639-649 (2000).

Kristensen, S., "Mechanisms of cell damage and enzyme release," *Danish Med. Bull.*, 41(4):423-433 (1994).

McAllister, Jr., H., "Histologic Grading of Cardiac Allograft Rejection: A Quantitative Approach," *J. Heart. Transplant*, 9(3):277-282 (1990).

Pagano, R. and J. Weinstein, "Interactions of Liposomes with Mammalian Cells," *Ann. Rev. Biophys. Bioeng.*, 7:435-468 (1978).

Palombo, J., J. Bowers, M. Clouse, A. McCullough, et al., "Hepatic utilization of exogenous nucleotide precursors for restoration of ATP after cold ischemia in rats," *Amer. J. Clin. Nutr.*, 57:420-427 (1993).

Pearson, M. and G. Rohrmann, "Transfer, Incorporation, and Substitution of Envelope Fusion Proteins among Members of the *Baculoviridae, Orthomyxoviridae, and Metaviridae* (Insect Retrovirus) Families,"0 *J. Virology*, 76(11):5301-5304 (2002).

Puisieux, F, E. Fattal, M. Lahiani, J. Auger, P. Jouannet, P. Couvreur, and J. Delattre,"Liposomes, an interesting tool to deliver a bioenergetic substrate (ATP) in vitro and in vivo studies," *J Drug Target* 2:443-448 (1994).

Reimer, K., R. Jennings, and M. Hill,"Total Ischemia in Dog Hearts, in Vitro," *in* "High Energy Phosphate Depletion and Associated Defects in Energy Metabolism, Cell Volume Regulation, and Sarcolemmal Intergrity." *Circ. Res.*, 49:901-911 (1981).

Schiffelers, R., G. Storm, and I. Bakker-Woudenberg, "Liposome-encapsulated aminoglycosides in pre-clinical and clinical studies," *J. Antimicrob. Chemotherap.*, 48:333-344 (2001).

Siegel, N., W. Glazier, I. Chaudry, K. Gaudio, et al., "Enhanced recovery from acute renal failure by the postischemic infusion of adenine nucleotides and magnesium chloride in rats," *Kidney Int'l*, 17:338-349 (1980).

Stringham, J. Southard, G. Anderson, and F. Belzer, "Mechanisms of ATP Depletion in the Cold-Stored Heart," *Transplantation Proc.*, 23(5):2437-2438 (1991).

Trigiante, G. and W. Huestis, "Selective virus-mediated intracellular delivery of membrane-impermeant compounds by means of plasma membrane vesicles," *Antiviral Res.*, 45:211-221 (2000).

Whitman, G., R. Kieval, L. Wetstein, S. Seeholzer, et al., "The Relationship between Global Myocardial Ischemia, Left Ventricular Function, Myocardial, Redox State, and High Energy Phosphate Profile. A Phosphorous-31 Nuclear Magnetic Resonance Study," *Surg. Res.*, 35:332-339 (1983).

Venkatachalam, M., J. Kriesberg, J. Stein, M. Lifschitz, "Salvage of Ischemic Cells by Impermeant Solute and Adenosinetriphosphate," *Lab. Investig.*, 49(1):1-3 (1983).

* cited by examiner

ATP-SUV        Control

DIRECT CELLULAR ENERGY DELIVERY SYSTEM

RELATED APPLICATIONS

This application claims priority to U.S. provisional application Ser. No. 60/380,762, FUSOGENIC LIPID VESICLES, to William D. Ehringer and Sufan Chien, filed May 14, 2002, which is incorporated herein by reference in its entirety.

BACKGROUND

ATP is the fuel that powers all cells-animal, plants, bacteria, fungi, etc. Such as a car without gas, humans and other creatures with an empty ATP "tank" do not go. In fact, they die. The energy derived from the breakdown of nutrients is ultimately conserved in the high energy phosphate bonds of ATP. When these bonds are broken, they provide accessible energy to cells, tissues, organs and organ systems. Cells constantly synthesize and metabolize ATP. ATP can be produced either aerobically through oxidative phosphorylation, with oxygen as the terminal electron acceptor and yielding carbon dioxide ($CO_2$) and water as by-products, or anaerobically during glycolysis. While glycolysis can provide energy to cells, the supply is limited because the cellular environment becomes acidic, injuring the cell and inhibiting ATP production.

The vascular circulatory system delivers a continuous supply of energy that is derived from oxygen and nutrients. In the vasculature, a barrier of endothelial cells separates the cells being fed from the vessel lumen. To reach individual cells, oxygen and nutrients must pass through the endothelial lining into the interstitial space to deliver oxygen and nutrients. This oxygen supply can be cut off or reduced as a result of disease or trauma. For example, myocardial infarction (heart attack), stroke, hypotension and severe trauma, such as severing a carotid artery in an automobile accident, result in loss of oxygen, leading to the loss of homeostasis, and possibly resulting in death.

When blood supply is re-established after an ischemic event, an event that results in the loss of oxygen and nutrients to tissue, ischemia-reperfusion injury can occur. As the cells attempt to synthesize ATP, after reoxygenation, toxic metabolites are produced, such as free radicals, as the cells attempt to re-synthesize ATP. Ischemia is not only an injury- or disease-related phenomenon, but can be induced as a side effect of surgeries, such as aortic bypass, open heart surgery, major tissue reconstruction, tumor removal, intestinal resection and organ transplantation.

Ischemia represents an enormous challenge to successful tissue and organ transplantation. About 14,000 kidneys and 2500 hearts are transplanted in the United States each year. After removal, organs have a limited life span in the absence of nutrients and oxygen. Hearts must be transplanted within 4 to 6 hours after harvest, while kidneys must be transplanted within 72 hours. Because recipients are often far from donors, these short viability times hamper transplantation. Blood can be stored for about only 45 days at 4° C. and then must be discarded. More complicated is the acquisition of autologous blood in anticipation of surgery. Patients can usually only provide two units of blood in the 45 days. This amount does not suffice, because many surgical procedures use three, four or more units of blood.

Several attempts have been made to overcome or inhibit the detrimental effects of low oxygen supplies. These approaches include: (1) providing glycolytic intermediates to augment anaerobic ATP production; (2) reducing metabolic demand, such as storing cells, tissues and organs at 4° C.; and (3) adding ATP directly to the cells, tissues or organs. Supplying energy to cells would be preferably accomplished by direct administration of ATP; however, cells take up exogenous ATP poorly because they lack ATP receptors or channels. Furthermore, cell plasma membranes are hydrophobic, while ATP is hydrophilic, preventing the ATP from passing through. Introducing ATP into the blood stream is ineffective because ATP cannot cross the endothelial barrier, and ATP is prone to hydrolysis. Attempts to use liposomes to deliver ATP have been largely unsuccessful and inefficient (Arakawa et al. 1998, Puisieux et al. 1994). For example, Puisieux et al. constructed phosphatidyl choline, cholesterol and phosphatidyl serine lipid vesicles that encapsulated ATP, then incubated the vesicles with sperm cells, liver and brain tissue. Although some uptake was observed, controlled delivery matching metabolic demand for ATP was not achieved. When administered in the blood stream, liposomes are usually unable to breach the endothelial cell barrier; in addition, they usually do not have high rates of fusion with cellular membranes, a necessary event for the vesicle to deliver its ATP payload into the cells.

Animal cell plasma membranes contain four major phospholipids that represent greater than half of the total lipid: phosphatidylcholine, phosphatidylethanolamine, phosphatidylserine and sphingomyelin. Phosphatidylcholine and sphingomyelin are found mostly in the outer leaflet, while phosphatidylethanolamine and phosphatidylserine are found principally in the inner leaflet. The predominance of the negatively-charged phosphatidylserine and phosphatidylinositol in the outer leaflet results in a net negative charge on the cells surface. Plasma membranes help maintain cellular integrity and are selectively permeable. While some molecules are able to diffuse through membranes, most, including ATP, require other means to enter, such as transport proteins or channels.

SUMMARY

In a first aspect, the present invention is a vesicle, comprising ATP, and a phospholipid which is a stable vesicle former. The vesicle has a fusion rate of at least 20 vesicle fusions/second.

In a second aspect, the present invention is a vesicle, comprising a phospholipid which is stable vesicle former, and another polar lipid and/or PEG. The vesicle has a fusion rate of at least 20 vesicle fusions/second.

In a third aspect, the present invention is a vesicle, comprising ATP, and a phospholipid which is stable vesicle former. The phospholipid has the structure of formula (I')

$$X'\text{-}L'\text{-}Z'_2 \tag{I'}$$

wherein X' has a structure of formula (II')

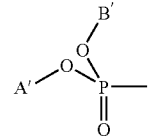

(II')

B' is a cation or an alkyl group,
A' is an alkyl group,
L' is an alkyl further missing two hydrogen atoms, and one Z' is E″, or the structure of formula (XI″),

(XI″)

wherein E″ is an alkyl or alkenyl, and
the other Z is E', or the structure of formula (XI')

(XI')

wherein E' is an alkenyl.

In a fourth aspect, the present invention is a vesicle, comprising a phospholipid which is stable vesicle former, and a polar lipid which is not a stable vesicle former and/or PEG. The phospholipid which is stable vesicle former has a structure of formula (I)

X-L-Z₂ (I)

wherein X is H, or has a structure of formula (II)

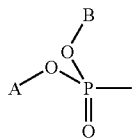
(II)

B is a cation or an alkyl group,
A is a H or an alkyl group,
L is an alkyl further missing two hydrogen atoms, and
each Z is independently H, E, or the structure of formula (XI),

(XI)

wherein E is an alkyl or alkenyl, and when one Z is H, the other Z is not H.

In a fifth aspect, the present invention is a method of delivering ATP to a cell, comprising contacting the cell with a vesicle. The vesicle comprises a phospholipid which is a stable vesicle former, and ATP. An amount of ATP delivered to the cell is sufficient to meet metabolic demand of the cell.

In a sixth aspect, the present invention is a method for treating a wound, comprising contacting the wound with a composition comprising a vesicle. The vesicle comprises a phospholipid which is a stable vesicle former, and ATP.

In a seventh aspect, the present invention is a composition comprising a vesicle, and becaplermin. The vesicle comprises a phospholipid which is a stable vesicle former, and ATP.

In an eighth aspect, the present invention is a method of improving the productivity of a bioreactor having at least one cell, comprising contacting the cell with a vesicle. The vesicle comprises a phospholipid which is a stable vesicle former, and ATP.

Definitions

"Alkyl" (or alkyl-or alk-) refers to a substituted or unsubstituted, straight, branched or cyclic hydrocarbon chain, preferably containing of from 1 to 20 carbon atoms. Suitable examples of unsubstituted alkyl groups include methyl, ethyl, propyl, isopropyl, cyclopropyl, butyl, iso-butyl, tert-butyl, sec-butyl, cyclobutyl, pentyl, cyclopentyl, hexyl, cyclohexyl, and the like. "Alkylaryl" and "alkylheterocyclic" groups are alkyl groups covalently bonded to an aryl or heterocyclic group, respectively.

"Alkenyl" refers to a substituted or unsubstituted, straight, branched or cyclic, unsaturated hydrocarbon chain that contains at least one double bond, and preferably 2 to 20 carbon atoms. Exemplary unsubstituted alkenyl groups include ethenyl (or vinyl), 1-propenyl, 2-propenyl (or allyl) 1,3-butadienyl, hexenyl, pentenyl, 1,3,5-hexatrienyl, and the like. Preferred cycloalkenyl groups contain five to eight carbon atoms and at least one double bond. Examples of cycloalkenyl groups include cyclohexadienyl, cyclohexenyl, cyclopentenyl, cycloheptenyl, cyclooctenyl, cyclohexadienyl, cycloheptadienyl, cyclooctatrienyl and the like.

"Alkoxy" refers to a substituted or unsubstituted,-0-alkyl group. Exemplary alkoxy groups include methoxy, ethoxy, n-propoxy, isopropoxy, n-butoxy, t-butoxy, and the like.

"Aryl" refers to any monovalent aromatic carbocyclic or heteroaromatic group, preferably of 3 to 10 carbon atoms. The aryl group can be bicyclic (i. e. phenyl (or Ph)) or polycyclic (i. e. naphthyl) and can be unsubstituted or substituted. Preferred aryl groups include phenyl, naphthyl, furyl, thienyl, pyridyl, indolyl, quinolinyl or isoquinolinyl.

"Amino" refers to an unsubstituted or substituted-NRR' group. The amine can be primary (—NH2), secondary (—NHR) or tertiary (—NRR'), depending on the number of substituents (R or R'). Examples of substituted amino groups include methylamino, dimethylamino, ethylamino, diethylamino, 2-propylamino, 1-propylamino, di(n-propyl)amino, di(iso-propyl)amino, methyl-n-propylamino, t-butylamino, anilino, and the like.

"Heterocyclic radical" refers to a stable, saturated, partially unsaturated, or aromatic ring, preferably containing 5 to 10, more preferably 5 or 6, atoms. The ring can be substituted 1 or more times (preferably 1, 2, 3, 4 or 5 times) with a substituent. The ring can be mono-, bi-or polycyclic. The heterocyclic group consists of carbon atoms and from 1 to 3 heteroatoms independently selected from the group consisting of nitrogen, oxygen, and sulfur. The heteroatoms can be protected or unprotected. Examples of useful heterocyclic groups include substituted or unsubstituted, protected or unprotected acridine, benzathiazoline, benzimidazole, benzofuran, benzothiophene, benzthiazole, benzothiophenyl, carbazole, cinnoline, furan, imidazole, 1H-indazole, indole, isoindole, isoquinoline, isothiazole, morpholine, oxazole (i. e. 1,2,3-oxadiazole), phenazine, phenothiazine, phenoxazine, phthalazine, piperazine, pteridine, purine, pyrazine, pyrazole, pyridazine, pyridine, pyrimidine, pyrrole, quinazoline, quinoline, quinoxaline, thiazole, 1,3,4-thiadiazole, thiophene, 1,3,5-triazines, triazole (i. e. 1,2,3-triazole), and the like.

"substituted" means that the moiety contains at least one, preferably 1–3 substituent (s). Suitable substituents include hydrogen (H) and hydroxyl (—OH), amino (—NH2), oxy (-0-), carbonyl (—CO—), thiol, alkyl, alkenyl, alkynyl, alkoxy, halo, nitrile, nitro, aryl and heterocyclic groups. These substituents can optionally be further substituted with 1–3 substituents. Examples of substituted substituents include carboxamide, alkylmercapto, alkylsulphonyl, alkylamino, dialkylamino, carboxylate, alkoxycarbonyl, alkylaryl, aralkyl, alkylheterocyclic, and the like.

DETAILED DESCRIPTION

Figure 1:
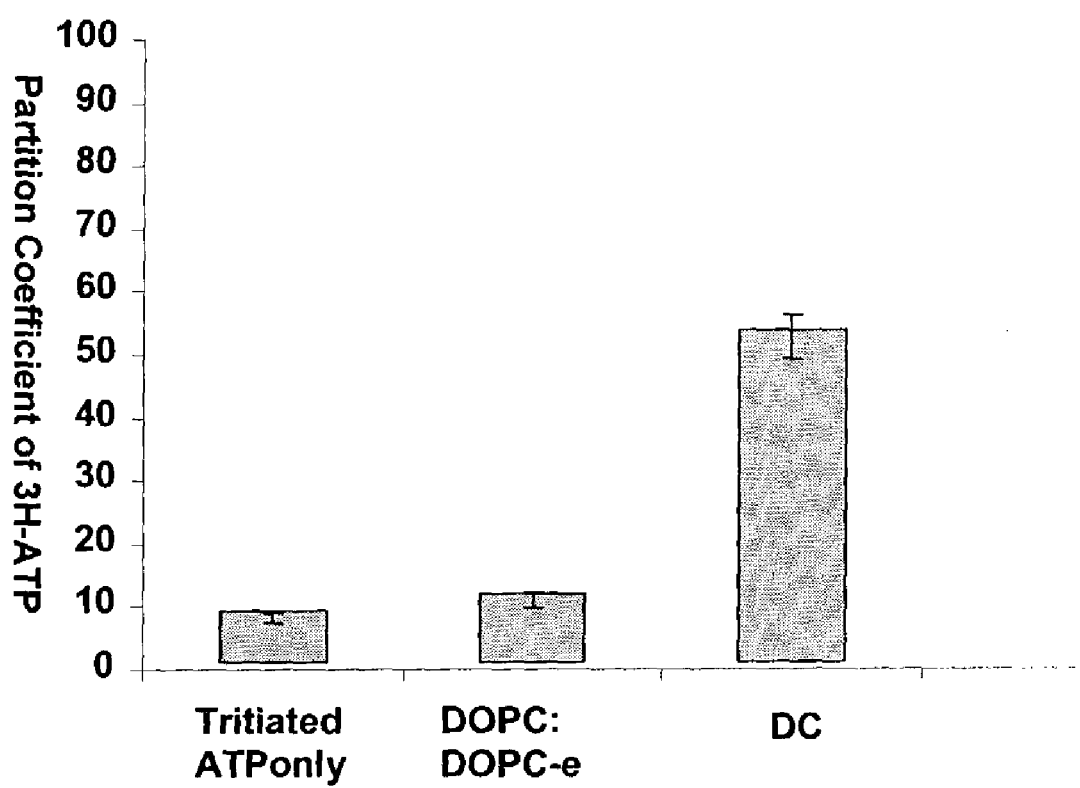
FIG. 1 shows the partition coefficient of ATP within human umbilical vein endothelial cells (HUVEC) after one hour.

The present invention makes use of the discovery that small lipid vesicles that are fusogenic with cellular bilipid membranes can encapsulate ATP and deliver the ATP directly to cells. The rate of ATP delivery is easily controlled by varying the lipid vesicle composition, as well as by other means, resulting in different fusion rates. In addition, the vesicle composition can be modulated to accommodate different modes of administration. For example, small lipid vesicles can be made such that when injected into the circulation, the vesicles fuse with endothelial cells, opening up gaps so that they can fuse efficiently with the target cells. To encourage or target fusion, other components may be added to the vesicles, such as certain polypeptides. By being loaded into a lipid vesicle, ATP is stabilized against hydrolysis.

The compositions and methods of the invention meet the requirements for effective ATP delivery to cells. Four requirements are necessary to effectively deliver ATP to cells: First, the ATP must pass through the cell membrane. Second, the amount of ATP must be delivered at a rate that meets basal metabolic demand. Third, the ATP-containing composition must be compatible with the route of administration. Finally, to be effective, ATP must enter the cells before hydrolysis.

Lipid vesicle membranes resemble plasma cell membranes; in addition, they are simple to make. Because they have an aqueous portion, lipid vesicles can encapsulate various solutions, including those containing ATP. Lipid vesicles can be made to fuse with cell membranes, allowing for the delivery of the lipid vesicles's contents.

The methods and compositions of the invention have a large array of uses, including treating hemorrhagic shock, heart attack, coronary heart disease, stroke, hypotension, severe trauma, wound healing, tissue and organ storage, cardiopulmonary resuscitation, and transplantation. In the case of severe trauma, the compositions of the invention may be administered in the field to minimize damage until medical help is available. The methods and compositions can also be used to prolong blood and platelet storage.

The following, not meant to limit the invention, is presented to aid the practitioner, although other methods, techniques, cells, reagents and approaches can be used.

Fusogenic Lipid Vesicles

Lipid vesicles resemble plasma membranes, and they can be made to fuse with cell membranes. Previous liposome studies have shown that four major types of interactions are observed between liposomes and cell membranes: adsorption to cell surface; endocytosis (the active taking-up of the liposome by phagocytic cells); lipid exchange (involving the transfer of individual lipid molecules between the liposome and the plasma membrane); and fusion (where the liposome membranes unite with plasma cell membranes). The interaction between lipid vesicles and cell membranes is probably similar to those between liposomes and cell membranes. Fusion provides the most attractive mechanisms since it allows for the direct introduction of vesicular contents into the cell. Adsorption or lipid exchange can occur when a vesicle is not very fusogenic and do not allow for the delivery of vesicular aqueous contents. Endocytosis can only occur in certain types of cells, such as leukocytes.

However, most liposomes and multilamellar vesicles are not readily fusogenic, mainly because the stored energy of the vesicle radius of curvature is minimal. But the small unilamellar vesicles of the present invention, which have a very tight radius of curvature, are very fusogenic. The average diameter of a small unilamellar vesicle (SUV) is 5 nm to 500 nm; preferably 10 nm to 100 nm, more preferably 20 nm to 60 nm, including 40 nm. This size allows vesicles to pass through the gaps between endothelial cells. Useful vesicles may vary greatly in size and are selected according to a specific application.

The compositions from which the vesicles of the present invention are formed contain a phospholipid which is a stable vesicle former, preferably together with another polar lipid, and optionally with one or more additional polar lipids and/or raft formers.

Polar lipids are organic molecules which have a hydrophobic end and a hydrophilic end, and contain at least six carbon atoms; they have the structure of formula (I), where X is a head group, L is a back bone group, and each Z is a fatty group. The two Z groups may be the same or different. A phospholipid is a polar lipid which has a head group of formula (II), where A and B are substituents of the head group.

The head group, X, may be any polar group, preferably a cationic, anionic or zwitterionic group, or H. More preferably X is a group of formula (II). Preferably, B is an cation, such as $Na^+$, $K^+$, or tetramethyl ammonium ion; or an alkyl group. Preferably, A is H, or an alkyl group; more preferably A is an alkyl group substituted with an amine; most preferably A is a group of formula (III), (IV), (V), (V) or (VII). It should be noted that throughout the specification, the formulas may show the structures in protonated form, but that they also include the unprotonated form (and visa versa); which form is present in any composition will depend on the exact pH of the composition, and the presence of water and/or appropriate counter ions.

The back bone group, L, is an alkyl further missing two hydrogen atoms (to give a total of three open attachment points), preferably an alkoxy, or amino substituted alkyl. Most preferably, L is a group of formula (VIII), (IX) or (X).

The fatty groups, Z, may be the same or different, and are H, an E group, or the structure of formula (XI), where E is an alkyl or alkenyl. Preferably, E is an unsubstituted straight chain alkyl or alkenyl, with 6–26 carbon atoms; more preferably E is a group of formula (XII), (XIII), (XIV), (XV), or (XVI). If one of the fatty groups is H, then the other must be different. If double bands are present, then cis configuration is preferable.

$$X—L—Z_2 \qquad (I)$$

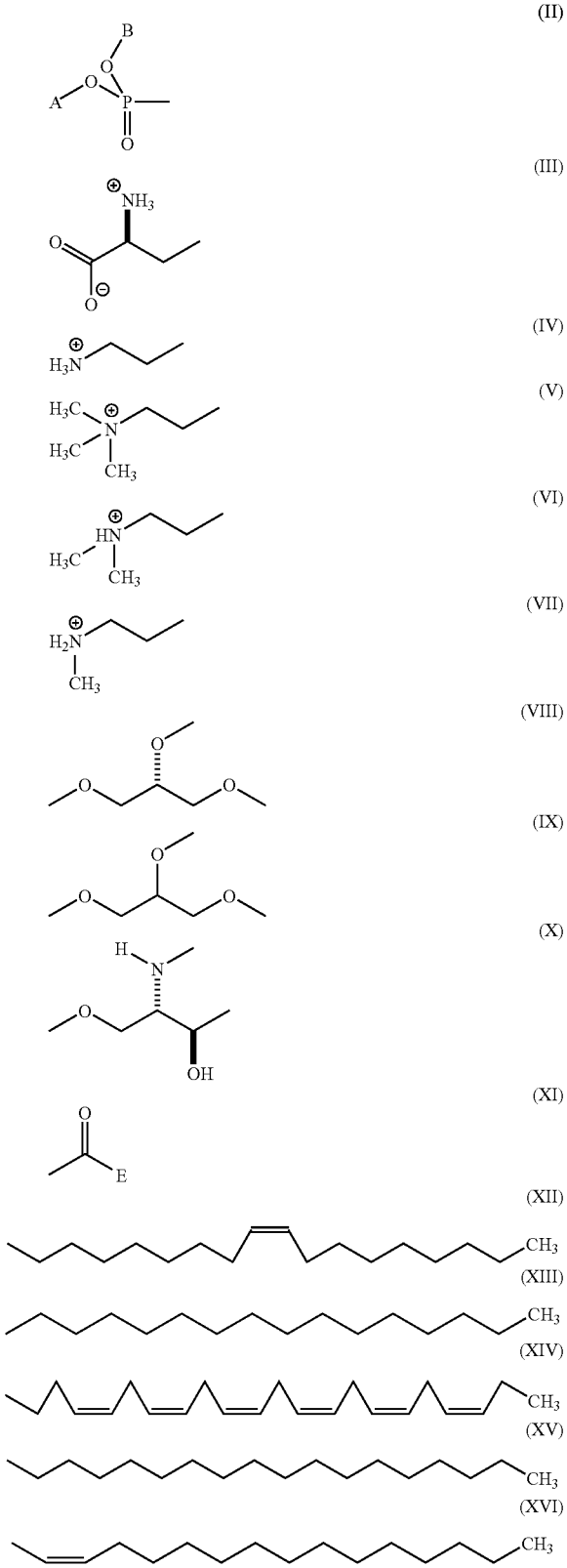

A phospholipid (or polar lipid) which is a stable vesicle former is a phospholipid (or polar lipid) that will form vesicles, at least 50% of which persist for at least one hour, when prepared as follows: the phospholipid is dissolved in chloroform and placed in glass test tube. Solvent is removed by evaporation under a steady stream of nitrogen, followed by air removal by subjecting the sample to vacuum for twelve hours. The dried lipid material is then re-hydrated in 10 mM $Na_2HPO_4$, for 60 minutes at a temperature above the lipid phase transition temperature; the desired final concentration is 25 mg/ml. The lipid mixture is then agitated by sonication with a microtip 450 watt sonicator used at a 40% duty cycle.

Preferably, in addition to the phospholipid which is a stable vesicle former, at least one other polar lipid is included, more preferably one or more polar lipids which are not stable vesicle formers.

A raft former is a compound which will sit within the lipid layer of a vesicle when the vesicle is in an aqueous solution, and will form or cause formation of discrete regions within the vesicle wall (also known as rafts). These discrete regions tend to destabilize the vesicle, increasing its fusogenicity. Examples of raft formers are cholesterol (formula XXIV), sphingomyelin, and proteins and polypeptides know to be membrane bound. Fusogenicity may also be enhanced by selecting polar lipids, which will result in a surface charge on the vesicle, which is the opposite of the charge of the Gouey-Chapman layer of the target cells (typically the Gouey-Chapman layer is positively charged).

Examples of polar lipids for use in the present invention include 1,2-dioleoyl-sn-glycero-3-phosphocholine(DOPC) (formula XVII; a stable vesicle former), 1-palmitoyl-2-oleoyl-sn-glycero-3-phosphate(POPA) (shown as the monosodium salt in formula XVIII), 1,2-dioleoyl-sn-glycero-3-ethylphosphocholine (DOPC-e) (shown as the chloride salt in formula XIX), 1,2-dioleoyl-sn-glycero-3-phosphoethanolamine (DOPE) (formula XX), 1,2-dioleoyl-sn-glycero-3-[phospho-1-serine](DOPS) (shown as the sodium salt in formula XXI), 1-palmitoyl-2-docosahexaenoyl-sn-glycero-3-phosphocholine (formula XXII; a stable vesicle former), a typical sphingomyelin (formula XXIII; cholesterol will form rafts when added to a vesicle formed from a mixture this sphingomyelin and DOPC), 1,2-dimyristoyl-sn-glycerol (formula XXV), and 1-palmitoyl-2-hydroxy-sn-glycero-3-phosphocholine (XXVI). Other polar lipids useful for the practice of the present invention include phosphatidyl serine (PS), phosphatidyl glycerol (PG), mixed chain phosphatidyl choline (MPC), phosphatidyl ethanol (PE), and phospholipids containing decosahexaenoic acids. Cit-DOPC and cit-DOPC-e are especially useful. Phosphatidylcholines, including those having a docosahexaenoic acid in the sn-1 and sn-2 positions (DHPC) may be used. Other diunsaturated lipids, such as diarachidonylphosphatidylcholine (for example 20:4 DOPC:DArPC), dilinolenoylphosphatidylcholine (for example 18:3 DOPC:DLnPC) are also useful. For example, DOPC may be mixed with increasing amounts of DLnPC, DArPC and DHPC during SUV preparation. Useful ratios include (DOPC:DLnPC, DArPC or DHPC) range from 1–1000:1, such as 25–500:1, including 1:1, 25:1, 50:1, 100:1, 500:1, and 1000:1. Combinations of phospholipids having large mean molecular areas can also be used, such as DOPC:DLnPC:DHPC. Diacylglyercol, a non-lamellar phase lipid, can also be mixed with DOPC. In addition, one can use polyethylene glycol (PEG) with weights of 20 repeats up to 4000 repeats.

Preferably, the ratio of the stable vesicle former phospholipid to the polar lipid which is not a stable vesicle former is 1:1 to 500:1, more preferably 10:1 to 100:1 (for example, 50:1). Examples include: DOPC/DOPC-e (1:1); DOPC/POPA (50:1) and DOPC/POPA (1:1).

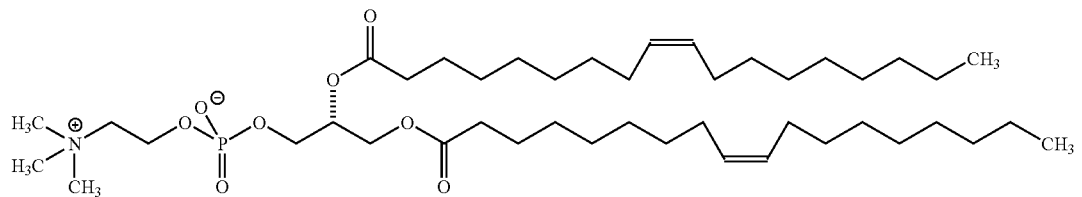
(XVII)
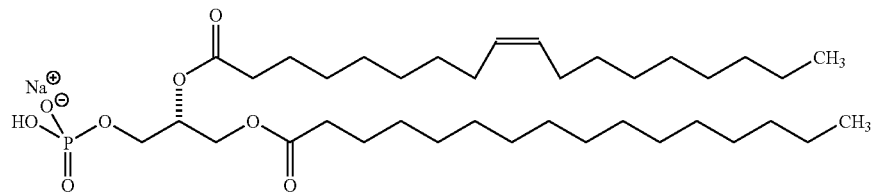
(XVIII)
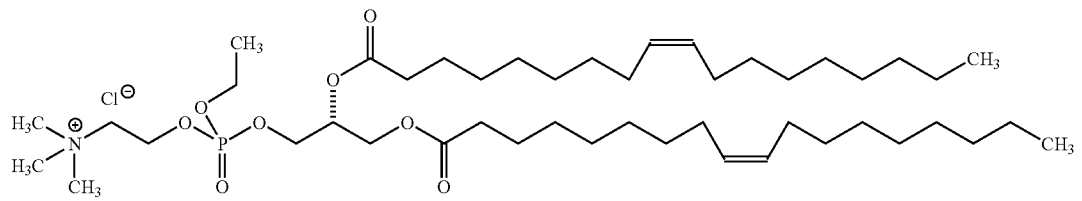
(XIX)
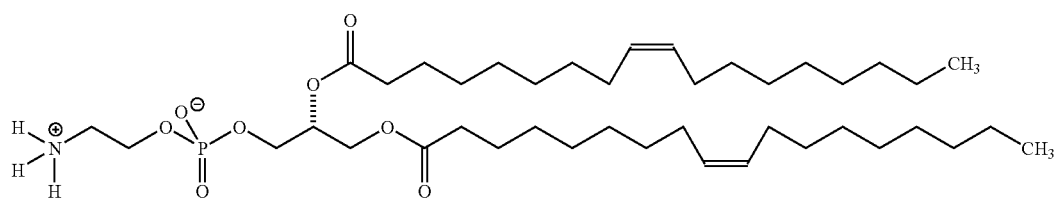
(XX)
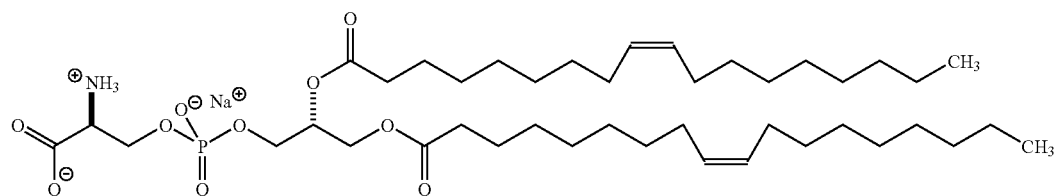
(XXI)
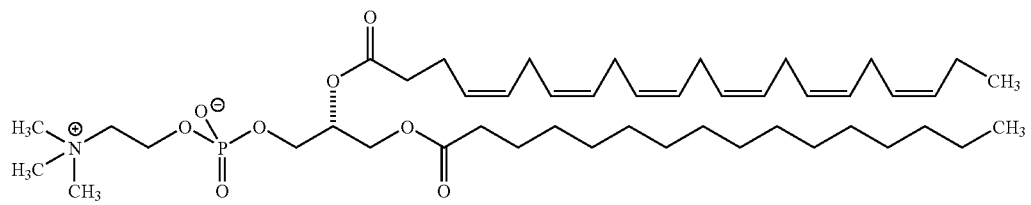
(XXII)
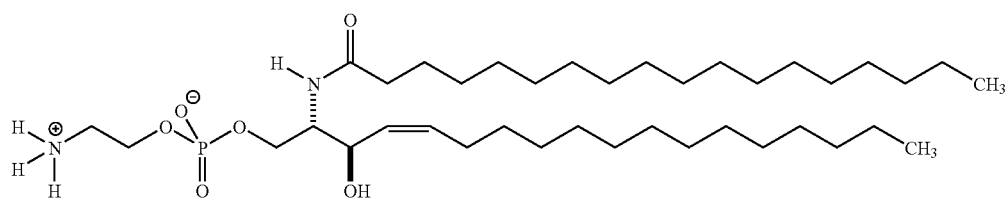
(XXIII)

-continued

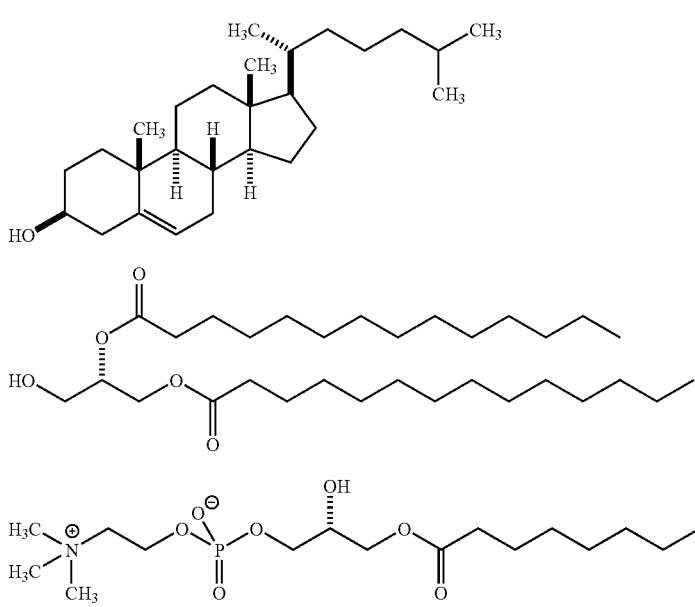

(XXIV)

(XXV)

(XXVI)

Lipid Vesicle Construction

To construct lipid vesicles, lipids are dissolved in chloroform or other appropriate organic solvent and placed in a vessel, such as glass test tube. Solvent is removed by evaporation under a steady stream of nitrogen or other neutral gas, followed by air removal, such as subjecting the sample to a vacuum for 0.1 to 48 hours, such as 1, 2, 3, 4, 5, 6, 7, 8, 9, 10, 11, 12, 15, 20, 24, 25, 30, 36, 40, 42 or 48 hours. Twelve hours usually suffices. The dried lipid material is then re-hydrated in an appropriate buffer, such as Hank's Balanced Salt Solution (HBSS) or 10 mM $Na_2HPO_4$, for 30–60 minutes at a temperature above the lipid phase transition temperature; the desired final concentration is usually approximately 1 to 30 mg/ml, typically around 25 mg/ml. The lipid mixture is then agitated. For example, sonication can be used; such as a microtip 450 watt sonicator used at a 40% duty cycle to create SUVs. The length of time of sonication depends on the amount of lipid material; in any case, sonication is stopped when no further decreases in percent transmission are observed or the correct vesicle size is achieved by analysis using a particle size analyzer. Lipids can be analyzed by UV spectroscopy and thin layer chromatography (TLC) to assess the extent of oxidation, if desired.

Other solutions may be used when rehydrating the dried lipids. These include those buffered with N,N-bis(2-hydroxyethyl)-2-aminoethanesulfonic acid (BES), bis(2-hydroxyethyl)amino-tris(hydroxymethyl)methane (BIS-Tris), N-(2-hydroxyethyl)piperazine-N'3-propanesulfonic acid (EPPS or HEPPS), glyclclycine, N-2-hydroxyehtylpiperazine-N'-2-ethanesulfonic acid (HEPES), 3-(N-morpholino) propane sulfonic acid (MOPS), Piperazine-N,N'-bis(2-ethane-sulfonic acid) (PIPES), sodium bicarbonate, 3-(N-tris(hydroxymethyl)-methyl-amino)-2-hydroxy-propanesulfonic acid) TAPSO, (N-tris(hydroxymethyl) methyl-2-aminoethanesulfonic acid (TES), N-tris (hydroxymethyl)methyl-glycine (Tricine), and tris (hydroxymethyl)-aminomethane (Tris). Other examples of suitable solutions include salt solutions, such as Alseverr's Solution, Dulbecco's Phosphate Buffered Saline (DPBS), Earle's Balanced Salt Solution, Gey's Balanced Salt Solution (GBSS), Puck's Saline A, Tyrode's Salt Solution, St. Thomas Solution and University of Wisconsin Solution.

Other components may be incorporated into SUVs to manipulate their fusion rates. For example, polypeptides that are involved in membrane fusion, such as fertilin, soluble N-ethylmaleimide-sensitive factor attachment protein receptors (SNAREs), SM (sec1/munc18) polypeptides (such as mammalian isoforms of Vps33p, Sly1p and Vps45p; (Jahn and Sudhof 1999)) and viral envelope fusion proteins, such as those from Human Immunodeficiency Virus (HIV; e.g., gp41), Semiliki Forest virus, and Influenza). The mammalian SNARE family includes the syntaxins (1A, 1B, 1C; 2 (and splicing variants); 3, 3A, 3B, 3C, 3D; 4; 5, 5A, 5B, 6, 7, 8, 10, 11, 12, 13 (maybe identical to 12); 16 (A, B, C); and 17), Hsyn 16, rbet1, GS15, GOS32, GOS28, Membrin, the SNAPs (25, 25a, 25b; 23, 23A, 23B; 29), vti1b, Synaptobrevins (1 and splicing variants; 2), Cellubrevin, VAMP4, VAMP5/6, Ti-VAMP, Endobrevin, Tomosyn and msec22b (Jahn and Sudhof 1999). Other amphiphilic peptides that destabilize membranes, even if their primary function is not to mediate membrane fusion, can also be used to promote fusion, such as annexins (Jahn and Sudhof 1999).

To target specific cells, polypeptides that either interact with a polypeptide specific to the targeted cell, such as a ligand-receptor interaction (at least in the area in which the SUVs are administered), or antibodies recognizing cell-specific antigens may be incorporated into SUVs. Other targeting polypeptides include those used during intercellular membrane transport and the Rab GTPase proteins. Viral fusion proteins can also be exploited as targeting molecules. Membrane bound substances, such as biotinylted lipids, and carbohydrates may also be used.

ATP Encapsulation

Typically, the magnesium salt of ATP is added at the time of lipid re-hydration. ATP concentration may vary and will depend on the application. Concentrations of ATP that are preferably used include 0.01 mM to 200 mM, preferably 0.1 mM, 1 mM, 2.5 mM, 5 mM, 7.5 mM, 10 mM, 25 mM, and 50 mM, and more preferably, 0.1 mM, 1 mM, 10 mM. The buffer containing the ATP should have a low protein content to decrease the chance of non-specific absorption of the lipid material. SUVs that contain ATP are referred to as ATP-SUV for convenience.

Encapsulation of ATP by SUVs can easily be assessed. For example, labeled ATP molecules (such that the label does not interfere with vesicle formation), such as radiolabeled ATP, preferably tritiated ATP is used. Radiolabels include $^{32}P$, and $^{3}H$ and are added when the lipids are re-hydrated after drying, prior to agitation. The solution is applied to a Sephadex G-25 column (or other suitable matrix) to remove non-encapsulated ATP. The effluent from the column is collected and assayed for the presence of vesicles. SUVs are usually eluted in the earliest fractions. Percent encapsulation is determined by quantifying the radioactivity in the vesicle and supernatant fractions, and determining the proportion of encapsulated ATP and multiplying by 100. Preferable encapsulation percentages range from approximately 1% to 10%.

Molecules other than ATP may be delivered to cells using SUVs, such as organic and inorganic molecules, including pharmaceuticals, polypeptides, nucleic acids and antibodies that interact with intracellular antigens.

Assay for Measuring SUV Fusogenicity

The fusion rate is a measure of the number of lipid vesicles that fuse with the HUVEC cells in a well/second (about $10^6$ cells), the assays has the following steps:

(1) HUVEC cells (American Type Culture Collection (ATCC); Manassus, Va. or BioWhittaker; Md.) are cultured;

(2) SUVs are prepared and loaded with a fluorescent probe, such as carboxyfluorescein;

(3) the SUVs are contacted to the cells to allow for fusion;

(4) at a selected time, any residual SUVs are removed; and (5) fluorescence is measured.

The presence and intensity of a fluorescent signal after removing the SUVs indicates the ability of the SUVs to fuse with the cell membranes and deliver the contents.

Human umbilical vein endothelial cells (HUVECs) is given as an example. The cells are grown to confluence on a standard 12-well culture dishes (for example, from COS-TAR; the number of cells is approximately $10^6$) in endothelial cell growth medium (EGM). The HUVECs are then washed 3 times with a buffer, such as HBSS. Prepared lipid vesicles (such as DOPC/DOPC-e (1:1); DOPC/POPA (50:1), DOPC/POPA (1:1), PS, PG, MPC, PE, cit-DOPC and cit-DOPCe), are loaded with 1 mM carboxyfluorescein. The vesicles are incubated with the cells for 120 minutes, assaying fluorescence at each 5 minute increment, at 37° C., 95% air/5% $CO_2$, after which time residual vesicles are removed by washing the cells with buffer. If negatively charged lipid vesicles are used, calcium (final concentration 0.1–10 mM) is added at the fusion step.

Cells are removed from the dish by treating with trypsin. Fluorescence is measured (excitation at 495 nm and emission of 520 nm) using a luminescence spectrophotometer or other suitable device.

The rate of fusion for ATP-SUV compositions is approximately 20 vesicle fusions/second to $8.0 \times 10^{11}$ vesicle fusions/second, including 500 to $1 \times 10^8$ vesicles fusions; 750,000 to $50 \times 10^7$ vesicle fusion/second; $5 \times 10^6$ to $1 \times 10^7$ vesicle fusions/second; including $1 \times 10^6$ to $8 \times 10^8$ vesicle fusions/second; $1 \times 10^7$ to $5 \times 10^8$ vesicle fusions/second; and $5 \times 10^7$ to $1 \times 10^8$ vesicle fusions/second. Examples of fusion rates are at least 100, 1000, $10^4$, $10^5$, $10^6$, $10^7$, $10^8$, $10^9$, $10^{10}$, and $10^{11}$ vesicle fusions/second. Some of these values were obtained experimentally at 37° C. using mixtures of DOPC and DOPC/DOPC-e and DOPC/POPA, with and without calcium, and using human endothelial cells.

Because the lipid composition of plasma membranes varies by cell type, the choice of cells for use in the assay is carefully considered, and should match as best the target cell type(s). For example, liver cell plasma membranes consist of about 7% phosphatidylethanolamine, while red blood cell plasma membranes contain 18% (Alberts et al. 2002). Primary culture cells, as well as cell lines (available from the American Type Tissue Collection (ATCC); Manassus, Va.) are useful, although primary cultures are preferred because of the likelihood that the plasma membrane lipid composition is altered in transformed cells. Cell types include pancreas, intestinal, immune system, neuronal (including those of the brain, eye, nose and ear), lung, heart, blood, circulatory (lymph and blood), bone, cartilage, reproductive, glandular, enamel, adipose, skin, and hepatic. Cell lines include those derived from these tissues, such as Madin-Darby canine kidney (MDCK), Chinese hamster ovary (CHO), HeLa, etc. Cells may be from other organisms, such as plants, fungi (including yeasts), and bacteria. Examples of fusion rates with these other cell types include at least 100, 1000, $10^4$, $10^5$, $10^6$, $10^7$, $10^8$, $10^9$, $10^{10}$, and $10^{11}$ vesicle fusions/second. Unless otherwise specified, fusion rates are with respects to HUVECs under the conditions specified above. Fusion rates with respects to other cell types is for about $10^6$ cell, with a buffer, such as HBSS, and the vesicles are incubated with the cells for 120 minutes at 37° C., 95% air/5% $CO_2$, after which time residual vesicles are removed by washing the cells with buffer.

Assays for Optimizing Fusion Rates

The assay for fusion rate can be further modified when optimizing the fusion rate of a particular vesicle composition with a particular cell type. For example, the lipid vesicle can contain a fluorescent or radioactive tracer that is part of the membrane bilayer of the vesicle.

Other fluorescent probes may also be used. These include fluorescein isothiocyanate; fluorescein dichlorotriazine and fluorinated analogs of fluorescein; naphthofluorescein carboxylic acid and its succinimidyl ester; carboxyrhodamine 6G; pyridyloxazole derivatives; Cy2, 3 and 5; phycoerythrin; fluorescent species of succinimidyl esters, carboxylic acids, isothiocyanates, sulfonyl chlorides, and dansyl chlorides, including propionic acid succinimidyl esters, and pentanoic acid succinimidyl esters; succinimidyl esters of carboxytetramethylrhodamine; rhodamine Red-X succinimidyl ester; Texas Red sulfonyl chloride; Texas Red-X succinimidyl ester; Texas Red-X sodium tetrafluorophenol ester; Red-X; Texas Red dyes; tetramethylrhodamine; lissamine rhodamine B; tetramethylrhodamine; tetramethylrhodamine isothiocyanate; naphthofluoresceins; coumarin derivatives; pyrenes; pyridyloxazole derivatives; dapoxyl dyes; Cascade Blue and Yellow dyes; benzofuran isothiocyanates; sodium tetrafluorophenols; and 4,4-difluoro-4-bora-3a,4a-diaza-s-indacene. The excitation wavelength will vary for these compounds. Lipid vesicles are made in the presence of the tracer in ratios such as 1:800 lipid/probe. Other useful ratios include 1:200 to 1:10,000, including 1:400, 1:500, 1:600, 1:700, 1:800, 1:900 and 1:1000.

Altering Fusion Rates

The fusion rate of any lipid vesicle can be altered by changing a variety of factors, such as temperature, ions, lipid concentration, lipid vesicle composition, flow rates, lipid vesicle size, etc. Altering the phospholipid formulation of SUVs can be used to maximize fusion rates as well as minimize toxicity. For example, to preserve organs for transplant or cells in suspension (such as blood), SUVs that have slower, delayed fusion rates are desirable. Such rates are obtained with vesicles consisting of only DOPC. On the other hand, if immediate raising of the intracellular ATP is crucial, as for stroke, heart attack or trauma sufferers, SUVs with very fast rates of delivery are desirable; DOPC/POPA compositions, for example, deliver sufficient ATP in less than five minutes (see Examples).

Four general approaches can be used to alter fusion rates by manipulating lipid composition:
(1) increasing electrostatic interactions;
(2) destabilizing membrane bilayers;
(3) increasing non-bilayer phases; and
(4) creating dissimilar lipid phases.

Increasing Electrostatic Interactions

Electrostatic interactions can be exploited to increase fusion rates. Phospholipids are classified according to their charge (cationic, anionic, and zwitterionic). Many of the cationic phospholipids, such as PE, and anionic phospholipids, such as phosphatidic acid (POPA), do not form closed vesicles at physiologic pH. However, anionic and cationic lipids mixed with zwitterionic phosphatidylcholines can form closed vesicles at physiologic pH.

The plasma membrane of most cells has a net negative charge. Because of this negative charge, there is a layer of counterbalancing ions, typically calcium, magnesium, sodium and potassium, which presents a net positive charge. Taking advantage of the electrostatic interaction between liposomes and plasma membranes, SUVs are engineered to have a net negative charge, thus maximizing cell-lipid vesicle fusion. However, some cell plasma membranes contain more cationic lipids which are counterbalanced by a anionic ion layer. In these situations, SUVs are engineered to have a net positive charge to maximize cell-lipid fusion.

Creating Dissimilar Lipid Phases

Plasma membranes contain lipid domains or rafts that are enriched in a particular lipid species. At the boundary of such a membrane raft are regions of dissimilar lipid species. These regions have the potential for instability, effecting how the membrane interacts with other membranes. Several phospholipids are known to increase lipid raft formation, including mixtures of phosphatidylcholines, sphingomyelin, and cholesterol. For example, DOPC, 18:0 sphingomyelin, and cholesterol are mixed in a 1:1:1 ratio during SUV preparation. Cholesterol preferentially partitions in the sphingomyelin phase, creating regions that are rich in DOPC and poor in cholesterol, and regions that are rich in sphingomyelin and rich in cholesterol.

Changing the physical parameters of fusion, temperature, concentration, ionic strength, and fusion period, can be used to affect fusion rates. By altering temperature, the free energy (G) of the system is altered, leading to different rates of fusion. Increasing lipid vesicle concentration also affects membrane fusion rates, especially at very high concentrations. The fusion period (length of fusion) and the number of fusion periods also affect the rate of delivery of the encapsulated contents of SUVs.

Temperature

ATP-SUV is incubated with tissues 5, 10, 15, 30, 60 or 120 minutes at the temperatures at which the tissues are being preserved (4° C.-hypothermia, 22° C.-room temperature, 37° C.-normothermia). Increasing the temperature of the vesicle solution leads to increased kinetic energy of the vesicles and hence increased capability to fuse. Temperature also affects the free diffusion of the vesicles.

Concentration on Vesicle Fusion

While intuitive that increased concentration leads to increased SUV content delivery, the rate of membrane fusion is not linear. Once SUV lipids occupy all of the available plasma membrane surface, further fusion is limited. The extent of fusion with the plasma membrane affects membrane volume and properties, such as ion permeability and lipid organization. Therefore, when administering SUVs, SUV concentration must be controlled so that the target cells are effectively treated.

Fusion Period

The length of time that fusion is allowed to occur helps to control the extent to which encapsulated substances are delivered. Preferable fusion periods are 1–180 minutes, such as 1, 5, 10, 30, 60, 120 and 180 minutes. To halt fusion, the vesicles are removed (such as by washing with a buffer), or the concentration of the administered vesicles is such that the vesicles are depleted at the end point of the desired time. Fusion may also be optimized such that the total delivery of the vesicles is controlled through one or multiple administrations. For example, if the target fusion period is 120 minutes, two 60 minute periods may be used, or four 30 minute, twelve 10 minute, or 24 five minute fusion periods. Provided that proper equipment is available, 1 minute or less fusion periods may also be accomplished, although these periods are often inconvenient and technically demanding.

Determining ATP Requirements of the Targeted Cells and Tissues

The optimum rate of ATP administration is that which approximates the basal metabolic demand for ATP of cells; this can be determined by any method known in the art. Oxygen consumption rates, pyruvate, glucose, lactate, and proton leak can be calculated, and from this data, the ATP consumption of the tissues is determined as ATP consumed/minute.

Tissue Oxygen Consumption

Samples of tissue are placed in a pre-cooled to −20° C. glass homogenizer. Ice cold isolation buffer, such as 200 mM sucrose, 70 mM KCl, 5 mM maleate and 40 mM Tris at pH 7.3, is added, and the tissue gently homogenized. The homogenate is briefly centrifuged to remove non-homogenized material. Five milliliters of oxygenation buffer is then placed in an oxygen meter and allowed to equilibrate to 37° C. The cells are placed in a YSI oxygen bath stirrer (Yellow Springs, Ohio) to a final protein concentration of 2–3 mg/ml. An oxygen probe is placed into the solution, and a YSI oxygen meter is used to measure the % oxygen in the solution. ADP is then added to the bath to achieve State 2 respiration rate, followed by glutamate addition, achieving State 3 respiration rate. Once the glutamate is consumed by the tissue, a final state of respiration is achieved, State 4. A plot of the State 3 respiration rate versus the amount of ADP that was added to the homogenate allows for the calculation of the phosphorus/oxygen (P/O) ratio. This value determines the amount of ATP the tissue can produce from ADP/minute, which is an index of the amount of ATP the tissue consumes/minute.

Membrane Potential and Proton Leak

Tissue samples are isolated and incubated with the membrane potential fluorescent probe MC540 (Sigma; St. Louis, Mo.). Changes in fluorescence of MC540 upon addition of various amounts of potassium is measured as an indice of membrane potential and proton leak as previously described (Brand, 1995).

Glucose, Pyruvate, and Lactate Levels

These metabolic intermediates are determined using standard methods or commercially-available analysis kits (such as those available from Sigma). The levels of these intermediates are adjusted to protein levels and are measured over a 120 minute time period.

Determination of ATP Consumption

From the rates of lactate, pyruvate, and glucose accumulation, oxygen consumption, and proton leak, it is possible to calculate all of the fluxes through the system by using reaction stoichiometries as described by Ainscow and Brand (1999).

Administration

Pharmaceutical Compositions

In many cases, ATP-SUV may be delivered as a simple composition comprising the ATP-SUV and the buffer with which it was made. However, other products may be added, if desired, such as those traditionally used as carriers in pharmaceutical compositions.

A "pharmaceutically acceptable carrier" includes any and all solvents, dispersion media, coatings, antibacterial and antifungal agents, isotonic and absorption delaying agents, and the like, compatible with pharmaceutical administration (Remington 2000). Preferred examples of such carriers or diluents include water, saline, Ringer's solutions and dextrose solution. Supplementary active compounds can also be incorporated into the compositions.

General Considerations

A pharmaceutical composition of the invention is formulated to be compatible with its intended route of administration, including intravenous, intradermal, subcutaneous, oral, inhalation, transdermal, transmucosal, and rectal administration. Solutions and suspensions used for parenteral, intradermal or subcutaneous application can include a sterile diluent, such as water for injection, saline solution, polyethylene glycols, glycerine, propylene glycol or other synthetic solvents; antibacterial agents such as benzyl alcohol or methyl parabens; antioxidants such as ascorbic acid or sodium bisulfite; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampules, disposable syringes or multiple dose vials made of glass or plastic.

If negatively charged lipid vesicles are used in the ATP-SUV compositions, calcium is included such that the final concentration at the site of fusion is preferably 0.1 mM-10 mM; including 0.1, 1, 2, 3, 4, 5, 6, 7, 8, 9 or 10 mM.

The ATP in ATP-SUVs is usually in equilibrium with the ATP in any solution surrounding the ATP-SUVs; typically only 1–10% of the total ATP is within the ATP-SUVs. The remaining ATP may bind to receptors, such as the purinoreceptor P2y, causing ions to flow out of the cells, and interfering with ion balance and homeostasis. Although the cells can usually reestablish ion balance and homeostasis, this consumes additional ATP. Therefore, particularly with tissue for which immediate restoration of function is desirable (for example, during organ transplantation, or limb reattachment), including in the composition one or more purinoreceptor P2y antagonists, is advantageous. The purinoreceptor P2y antagonists is preferably added to the composition after forming the vesicles, or just prior to administration, since the antagonists do not need to be within the SUVs. Examples of purinoreceptor P2y antagonists include pyridoxal 5-phoshpate, vitamin B6 (pyridoxal-5-phosphoric acid), and Reactive Blue 2 (1-amino-4-[[4-[[4-chloro-6-[[3(or 4)-sulfophenyl]amino]-1,3,5-triazin-2-yl] amino]-3-sulfophenyl]amino-9,10-dihydro-9,10-dioxo-2- anthracenesulfonic acid), and combinations thereof. The purinoreceptor P2y antagonists may preferably be used in a concentration of 0.1 to 250 micromoles/L, more preferably 1–100 micromoles/L.

Injectable Formulations

Pharmaceutical compositions suitable for injection include sterile aqueous solutions or dispersions for the extemporaneous preparation of sterile injectable solutions or dispersion. For intravenous administration, suitable carriers include physiological saline, bacteriostatic water, CREMOPHOR EL™ (BASF, Parsippany, N.J.) or phosphate buffered saline (PBS). In all cases, the composition must be sterile and should be fluid so as to be administered using a syringe. Such compositions should be stable during manufacture and storage and must be preserved against contamination from microorganisms such as bacteria and fungi. The carrier can be a dispersion medium containing, for example, water, polyol (such as glycerol, propylene glycol, and liquid polyethylene glycol), and other compatible, suitable mixtures. Various antibacterial and anti-fungal agents, for example, parabens, chlorobutanol, phenol, ascorbic acid, and thimerosal, can contain microorganism contamination. Isotonic agents such as sugars, polyalcohols, such as manitol, sorbitol, and sodium chloride can be included in the composition. Compositions that can delay absorption include agents such as aluminum monostearate and gelatin.

Sterile injectable solutions can be prepared by incorporating ATP-SUV in the required amount in an appropriate solvent with one or a combination of ingredients as required, followed by sterilization. Methods of preparation of sterile solids for the preparation of sterile injectable solutions include vacuum drying and freeze-drying to yield a solid containing ATP-SUV lipids and any desired ingredient (such as ATP) a sterile solutions.

Oral Compositions

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally. Pharmaceutically compatible binding agents, and/or adjuvant materials can be included. Tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, PRIMOGEL, or corn starch; a lubricant such as magnesium stearate or STEROTES; a glidant such as colloidal silicon dioxide; a sweetening agent such as sucrose or saccharin; or a flavoring agent such as peppermint, methyl salicylate, or orange flavoring.

Compositions for Inhalation

For administration by inhalation, the compounds are delivered as an aerosol spray from a nebulizer or a pressurized container that contains a suitable propellant, e.g., a gas such as carbon dioxide.

Transmucosal or Transdermal

Administration can be transmucosal or transdermal. For transmucosal or transdermal administration, penetrants that can permeate the target barrier(s) are selected. Transmucosal penetrants include, detergents, bile salts, and fusidic acid derivatives. Nasal sprays or suppositories can be used for transmucosal administration. For transdermal administration, the active compounds are formulated into ointments, salves, gels, or creams. Suppositories (e.g., with bases such as cocoa butter and other glycerides) or retention enemas for rectal delivery may also be prepared.

Carriers

In one embodiment, the active compounds are prepared with carriers that protect the compound against rapid elimination from the body, such as a controlled release formulation, including implants and microencapsulated delivery systems. Biodegradable or biocompatible polymers can be used, such as ethylene vinyl acetate, polyanhydrides, polyglycolic acid, collagen, polyorthoesters, and polylactic acid. Such materials can be obtained commercially from ALZA Corporation (Mountain View, Calif.) and NOVA Pharmaceuticals, Inc. (Lake Elsinore, Calif.), or prepared by one of skill in the art.

Dosage

Dosage is dictated by, and directly depends on, the unique characteristics of ATP-SUV which varies with different SUV lipid compositions, the particular desired therapeutic effect, and the route of administration. The specific dose level and frequency for any particular patient or application may be varied. Factors that should be considered, including (1) the temperature at which administration is made and at which fusion is permitted; (2) the ionic environment of the administration site and the ionic strength of the ATP-SUV composition; and (3) the length of time that fusion is permitted. Controlling these factors helps to control the extent to which the encapsulated substances, including ATP, are delivered.

When administering SUVs, SUV concentration is controlled to effectively treat the target cells while not inhibiting their function by saturating the plasma membranes with SUV lipids. Preferable concentrations of SUV, depending on lipid composition, target cell dispersion and volume to be administered may be 0.5 mg/ml-100 mg/ml, such as 0.5 mg/ml, 1 mg/ml, 5 mg/ml, 10 mg/ml, 20 mg/ml, 30 mg/ml, 40 mg/ml, 50 mg/ml, 60 mg/ml, 70 mg/ml, 80 mg/ml, 90 mg/ml and 100 mg/ml.

Vesicle fusion occurring via electrostatic interactions is significantly affected by changes in calcium and/or magnesium concentrations, and to a lesser extent, changes in sodium and/or potassium concentrations. Modulating these ion concentrations either in the compositions used to administer ATP-SUV or in compositions administered to a target site before or after ATP-SUV administration, affect dosage considerations. Preferably, ion concentrations of 0.01 mM to 1 mM, including 0.1 nM, 1 nM, 100 nM, 100 nM, 1000 nM, 10 micromole/L, and 100 micromoles/L are used. Combinations of these and other ions may also be used.

Regimes of chronic administration or single dosing can be used and are chosen according to the type of treatment, administration route, the vesicles themselves. Preferable fusion periods include 1–180 minutes, such as 1, 5, 10, 30, 60, 120 and 180 minutes. To halt fusion, the ATP-SUV is removed (such as by washing with a buffer), or the concentration of vesicles is such that the vesicles are depleted at the end point of the desired time. Fusion can also be optimized such that the total delivery of the vesicles is controlled through one or multiple administrations. For example, if the fusion period is 120 minutes, two 60 minute periods may be used, or four 30 minute periods, twelve 10 minute periods, or 24 five minute fusion periods.

Uses for ATP-SUV

Because of the universal cellular requirement for ATP, ATP-SUV and other SUV/ATP compositions have a broad array of applications that span the biological kingdoms.

Blood

Blood can be stored under refrigeration for about 45 days before the red blood cells become nonviable. Red blood cells typically survive in circulation for about 120 days, after which the spleen and liver remove and destroy them. Thus if nonviable cells are transfused, they likewise are removed immediately from circulation.

The addition of ATP-SUV or other SUV-encapsulated ATP compositions to collected blood sustains the red blood cells longer, increasing viable storage time and the likelihood that the cells will remain in circulation and not destroyed.

The lipid compositions may be altered to optimize ATP delivery. For example, because blood is stored at 4° C., metabolic demand for ATP will be low. Even though the fusion rate of SUVs will also be slowed at this temperature, the rate may be too high for viable storage and SUV lipid compositions are derived to better match the metabolic demands of the blood cells.

When whole collected blood is stored in contact with the compositions of this invention, the white blood cells and platelets will also benefit and remain viable longer.

Sustaining Amputated Body Parts for Replantation

After the (usually inadvertent) amputation of a body part, the success of replantation depends in large part on the ability of the appendage to survive apart from its owner. The longer the ischemic time, the less likelihood that replantation results in a functional appendage, or even success of any kind at all.

In one example, the major feed artery of a recovered severed limb is cannulated for perfusion. The limb is perfused with the ATP-SUV every 4 hours, or as determined necessary due to changes in tissue ATP levels. The arterial pressure of the limb is monitored during perfusion to decrease the chance of flow-induced injury, and to monitor the overall preservation of the severed limb—higher perfusion pressures may indicate limb morbidity. Following the preservation period, the limb is flushed with Ringers or other suitable solution to remove traces of ATP-SUV. The limb is then surgically reattached using well-known methods. External indices of limb function after anastomoses are evaluated (color, evidence of microthrombi, temperature, pulse, oxygen saturation, Doppler flow measurements) to monitor success. Prior to and following replantation, heparin is applied and antibiotic therapy is commenced to reduce the likelihood of infection.

Heart Arrest

The ATP-SUV is injected into the heart by intravenous or intracardiac injection, immediately or as soon as possible following the hypoxic episode. The SUV lipid compositions are manipulated so that ATP delivery is carefully matched to the metabolic demand of heart tissue, maximizing heart performance. ATP-SUV may be constantly perfused into the heart at physiologic conditions until such time the danger of ischemia has passed.

Delivering ATP for Organ Preservation

Organs (e.g., hearts, liver, lungs, kidney or pancreas) are removed from the donor, and the major feed artery into the organ is cannulated. The blood in the organ is flushed from the organ using saline, Ringers solution or other suitable solution. ATP-SUV is added to regular preservation solutions or to buffer, and gently perfused ($\geq 80$ mm Hg) into the organ, the frequency of which will depend on the organ.

The same ATP-SUV can be used in the animal laboratory setting. For example, a Lagendorff heart (or other organ) perfusion apparatus is used. The aorta is cannulated and the heart is placed into a perfusion chamber. The heart is perfused with an oxygenated perfusate to which ATP-SUV has been added. A high concentration potassium solution may be injected to cause cardiac arrest. A cardioplegia with ATP-SUV can be used during the preservation period. The heart can be reprofused for functional studies or can be transplanted after ischemic preservation.

Delivering ATP Systemically

ATP-SUV can be administered to organisms for a variety of reasons. For example, ATP-SUV can be used to supplement energy in the body (preferred administration routes are oral, topical and inhaled), or it can be used to decrease the reliance upon oxygen for the whole body (preferred administration route in this case would be intravenously). When ATP-SUV is administered to animals by continuous infusion via the carotid artery, heart rates and blood pressure decrease and respiration ceases. The animals can be resuscitated, even after 9 minutes of hypoxia (see Examples).

ATP-SUV for Wounds

Because blood flow to wounds is diminished, less oxygen is available to the cells in and around the wound. The decrease in oxygen delivery results in a decrease in ATP production, which slows many cellular events necessary for wound healing, including protein and nucleic acid synthesis, ion channel function, signal transduction, and locomotion.

ATP-SUV is applied to the wound as necessitated by the extent of healing or the ATP consumption of the wound. For example, to provide the border cells of the wound sufficient ATP to accelerate wound closure, ATP-SUV may be applied preferably 1–12 times per day, such as 1, 2, 3, 4, 5, 6, 7, 8, 9, 10, 11 or 12 times/day. Preferably, the ATP-SUV is placed directly over the wound in a specially designed applicator which keeps the water-based ATP-SUV in direct contact with the wound border cells. Alternatively, the ATP-SUV may be applied topically as a cream or other topical pharmaceutical composition.

ATP-SUV may also be combined with healing compositions already available to further enhance healing. For example, ATP-SUV can be combined with becaplermin, as found in Regranex®. Other wound-treating components besides becaplermin include antiseptics, antibiotics, and anesthetics. The term "wound-treating component" does not include SUVs.

ATP-SUV for Hemmorhagic Shock

Hemmorhagic shock results from losing large amounts of blood, caused by internal or external injuries. Because the blood supply is insufficient, the subject often becomes hypotensive, resulting in organ failure and imminent death.

To counter the effects of hemmorhagic shock, ATP-SUV is infused intravenously as a supplement to blood transfusion. The ATP-SUV can then be decreased as whole body oxygenation improves.

ATP-SUV for Platelet Storage

Platelets have a shelf-life of about 5 days, after which they must be discarded. The loss of platelet function is partly due to loss of ATP.

Isolated platelets are given ATP-SUV as needed to maintain intracellular ATP levels. The shelf life of the platelets is then extended. ATP-SUV is suspended in a suitable solution for platelet storage, such as saline. The SUV lipid compositions may be altered to optimize ATP administration. For example, because platelets are stored at room temperature (22–24° C.), metabolic demand for ATP will be lower than at physiologic temperature (37° C.). Even though the fusion rate of SUVs will also be slowed at this temperature, the rate may be too high for viable storage and SUV lipid compositions are derived to better match the metabolic demands of the platelets.

ATP-SUV for Organ and Tissue Engineering

Tissues can now be grown in vitro with great efficiency. However, such tissues lack a vasculature to connect to the blood supply. ATP-SUV helps overcome this defect.

ATP-SUV can be used to selectively preserve a blood vessel network derived from isolated tissue, such as a skeletal muscle. The lipid composition of the ATP-SUV is made such that the ATP-SUV does not easily escape from the blood vessels. Administration of ATP-SUV maintains the vasculature, but not the parenchyma, which dies. The intact vasculature is then be seeded and cultured under appropriate conditions with stem cells that are competent to differentiate into specific tissues. In vitro-produced tissues that can be vascularized in this manner include liver, pancreas, heart, lung and spleen.

Alternatively, organs already undergoing in vitro construction can be partially vascularized using this same approach, except the vasculature is harvested and treated after the organ cells have started growing.

ATP-SUV During Surgery

Decreased blood flow and oxygen are inflicted during major surgical procedures. ATP-SUV can be administered to the whole body or to the areas which are involved in surgical procedures to minimize any damage from ischemia or hypoxia. Examples of surgeries in which ATP-SUV is useful include coronary bypass, open-heart surgery, free flap transfer, and some plastic surgery procedures.

In some surgeries, paralysis sometimes results because the spinal cord does not receive sufficient oxygen during the procedure. This occurs mainly in aortic aneurysm resection. The application of ATP-SUV to the affected areas or administered intravenously allows surgeons more time to work, and decreases the likelihood of loss-of-oxygen-induced injuries, and results in decreased morbidity.

ATP-SUV for Stroke

Currently, administration of a high glucose solution immediately following a stroke is used to decrease the effects of decreased blood flow to the brain, The glucose is expected to increase neural cell ATP levels and decreases neural cell death. However, this goal is difficult to achieve when oxygen supply is limited. ATP-SUV would provide neural tissues with ATP more efficiently.

ATP-SUV for Respiratory Problems

Many respiratory aliments decrease the quality of life, and often lead to death. In these cases, the major leading cause of death is a lack of oxygen in the blood, resulting in tissue and organ death. Subjects are infused with ATP-SUV to decrease the effects of decreased blood oxygen levels.

ATP-SUV for Cancer Patients

End-stage cancer patients die from resulting complications. Because cancer or therapies have weakened them, cancer patients often die from pneumonia. The weakness results from either the cancer cells usurping valuable metabolic resources and thus impoverishing healthy cells, or non-cancer healthy cells being destroyed during therapy, or both. Cancer patients are administered ATP-SUV daily to supplement whole body ATP levels and thus decrease the effects of the cancer cells appropriating metabolic resources. By administering ATP-SUV, sequellae from cancer are decreased, and life expectancy is extended.

ATP-SUV for Chemical Poisons

Cyanide and other chemicals that block mitochondrial ATP production or otherwise decrease cellular ATP production can be thwarted by using ATP-SUV. ATP-SUV maintains cell and tissue viability and function when bathed in cyanide—ATP-SUV increases cytosolic ATP in the absence of mitochondrial ATP production. ATP-SUV can be used as an antidote for cyanide and for other poisons that act in a similar manner as cyanide. ATP-SUV can also be used to decrease the effects of carbon monoxide poisoning.

ATP-SUV for Delivery of Proteins, Carbohydrates, Oligonucleotides, and Other Drugs The highly fusogenic lipid vesicles which comprise ATP-SUV can be made in the presence of water soluble and membrane bound proteins, carbohydrates, oligonucleotides, and other drugs, so that efficient delivery is obtained to the cytosol or to the cell membrane any of the aforementioned substances. This method of drug delivery circumvents many traditional problems, and (1) allows for the introduction of pharmaceuticals that are membrane impermeable, thus greatly expanding the range of pharmaceuticals that can be used, as well as increasing the efficacy of those that have a low rate of membrane penetration; and (2) allows for the incorporation of polypeptides and carbohydrates directly into cell membranes. This last advantage allows, for example, replacement therapies that circumvent uncertain gene therapy approaches. For example, if a subject lacks a receptor on a cell, that receptor can be incorporated into ATP-SUV SUVs and administered appropriately.

These methods mimics those methods that introduce ATP into cells, except that the SUVs are charged with either the substance within the vesicle, and/or membrane-incorporated molecules.

ATP-SUV for Other Low Oxygen Situations

Underwater diving, space travel, high altitudes, and other situations where oxygen is rare can lead to decreases in oxygen delivery to the body. To compensate for the oxygen deficit, ATP-SUV is administered intravenously, orally, or by inhalation.

ATP-SUV for Meat Preservation

In addition to its uses in tissue and organ preservation, and animals and patients, ATP-SUV can keep cells in meat alive in the absence of oxygen. After slaughter, the animal is bled and residual blood is flushed from the carcass. ATP-SUV is infused into the animal via the carotid or other large artery, filling the vasculature with ATP-SUV. The animal is then shipped with the ATP-SUV in place, keeping the cells of the animal alive and thus extending the shelf life of the meat, much as ATP-SUV extends the shelf life of blood. Since ATP-SUV makes use of endogenous components, the taste and texture of the meat is not affected.

ATP-SUV for Plants

Plants utilize photosynthesis in order to sustain life and growth. Photosynthesis can be divided into two reactions: the light reaction, which harvests energy from sunlight and converts it to chemical energy, ATP and the reduced form of nicotainamide adenine dinucleotide phosphate (NADPH); and the dark reaction, which uses ATP and NADPH to fix $CO_2$.

Plants are provided with ATP-SUV via either the root system or applied directly to the leaves, stems, flowers, meristems or other plant parts. ATP-SUV delivers the ATP necessary for the dark reactions to the plant cells. The delivery of ATP using ATP-SUV reduces or by-passes the need for sunlight, enabling them to grow in the dark or under less-bright conditions. In addition, the ATP-SUV increases plant growth and sustains plant life, important aspects to fresh vegetables at market, the cut-flower industry, and hydroponic gardening.

ATP-SUV for Bioreactors

The major limiting factor for bioreactor productivity is that bacteria and yeast, the primary producers of these substances, must have sufficient substrate to make ATP. Thus, the number of bacteria or yeast is limited in any one culture. ATP-SUV is infused into the bioreactor to increase the number of microorganisms, increasing output of the bioreactor. This application is not limited to bacteria and fungi, since cultured insect, animal, plant and other eukaryotic cells have the same requirement for ATP production.

EXAMPLES

The following examples are provided to illustrate the invention. Those skilled in the art can readily make insignificant variations in the compositions and methods of this invention. The examples are not meant to limit the invention in any way.

Example 1

Construction of Lipid Vesicles

Vesicles were constructed from 1,2-dioleoyl-sn-glycero-3-phosphocholine (DOPC); 1,2-dioleoly-sn-glycero-3-ethylphosphocholine (DOPC-e) and 1-palmitoyl-2-oleoyl-sn-glycero-3-phosphate (POPA) lipids. (all from Avanti Polar Lipids; Alabaster, Ala.). The lipids were used without further purification. After dissolving the lipids in chloroform and placed in a glass test tube, the chloroform was removed by evaporation under a steady stream of nitrogen gas, followed by overnight vacuum pumping. The dried lipid material was re-hydrated in HBSS experimental buffer (Sigma; St. Louis, Mo.) above its phase transition temperature (25° C.) for 30 minutes. Two glass beads were added to the buffer/lipid mixture, and the suspension vortexed for five minutes to create multilamellar vesicles. The milky solutions was then sonicated using a microtip Branson Sonifier 450, with the microtip placed in the test tube. The vesicles were then sonicated for five minutes at level 5 with a 40% duty cycle to create small unilamellar vesicles (SUVs).

Example 2

Encapsulation of ATP

To demonstrate incorporation of ATP into the vesicles of Example 1, 30 µCi of $^3$H-ATP (Amersham; Arlington Heights, Ill.) was added to the experimental buffer prior to creating the multilamellar vesicles. The suspension was passed over a Sephadex G-25 (Sigma) column (1 cm×40 cm) to remove the non-encapsulated ATP. The vesicles were collected in the first 50 ml of the effluent. The percent encapsulation was determined by measuring the radioactivity contain within the vesicles and in the supernatant by liquid scintillation counting. Vesicles comprising DOPC, DOPC:DOPC-e (1:1), DOPC:POPA (50:1) and DOPC:POPA (1:1) all gave approximately the same percent encapsulation of ATP, varying between 1 to 2.5% of the original amount of ATP in solution.

Example 3

Rate of Fusion of Vesicles to HUVEC and Release of Encapsulated Contents into the Cytoplasm To determine the fusogenic rate of SUVs, SUVs were loaded with a fluorescent probe, presented to cells in vitro, washed, and then analyzed for cellular fluorescence.

Human umbilical vein endothelial cells (HUVEC) were purchased from BioWhitaker (Walkersville, Md.) at passage I and cultured until passage 8, after which they were no longer used. HUVEC were grown endothelial cell growth medium (EGM; BioWhitaker) to confluence on 12-well culture dishes in EGM medium. The HUVEC were then washed 3 times with HBSS. Lipid vesicles were made as in Example 1, but 1 mM carboxyfluorescein was loaded into the vesicles. The vesicles were then incubated with the cells for either 5, 10, 30, 45, 60, 90, 120 or 240 minutes at 37° C. in a humidified $CO_2$ incubator, after which the vesicles were washed from the cells, and the cells removed from the dish by gentle treatment with trypsin. The fluorescence of carboxyfluorescein in the HUVEC was measured using a Perkin-Elmer LS5OB Luminescence Spectrophotometer (Wellesly, Mass.), using an excitation of 495 nm and emission of 520 nm. In some experiments, cells were not trypsinized, and photomicrographs of the cells were taken in order to demonstrate the homogeneity of the fusion event. The range of fluorescent units (FUs) for this experiment was 0 to 450 units. The rate of fusion highly depended on the lipid composition of the SUVs. DOPC showed little or no fusion at all for the first 30 minutes, after which the fusion rate became logarithmic, reaching approximately 350 FUs. In contrast, DOPC:DOPC-e (1:1) gave a much faster initial rate of fusion and a slower final rate of fusion (approximately 35 FUs at 5 minutes; approximately 100 FUs at 120 minutes). The fastest rate of fusion was found using DOPC:POPA (1:1), which showed significant delivery of ATP within 5 minutes. As designed, the fusion rate of the three vesicles can be characterized as fast, medium and slow.

One issue which was resolved was whether the vesicles were actually fusing with the cells or simply aggregating on the cell surface. To examine this, HUVEC exposed to lipid vesicles and not removed from the culture wells were examined for the distribution of fluorescence by fluorescent microscopy. Cells exposed to all three compositions showed diffuse fluorescence throughout the cells after 5 minutes rather than punctate fluorescence, which would have suggested that lysosomes were sequestering the vesicles, thereby preventing cellular access to the carboxyfluorescein. Alternatively, the vesicles were aggregating on the cell surface. These results demonstrate that lipid vesicles fused to the cells and released the encapsulated contents within the cytoplasm rather than aggregating on the cell surface or being sequestered by lysosomes.

To determine if ATP is also introduced into cells like carboxyfluorescein, vesicle fusion and release of ATP into HUVEC was followed using the $^3$H-ATP-containing vesicles of Example 2. The vesicles were incubated with HUVEC for either 5, 10, 15, 30, 45, 60, 90, 120, or 240 minutes. The result shown in FIG. 1 is the partition coefficient of ATP inside the cells after 1 hour. DOPC/POPA gave the largest percent incorporation at this distant time period, followed by DOPC/DOPC-e, then $^3$H-ATP only, without vesicles. When the cells were washed repeatedly there was a significant change in the radioactivity of the cells. DOPC showed a slight but significant decrease in radioactivity; DOPC/DOPC-e showed no decrease in radioactivity after repeated washes, while free $^3$H-ATP showed a complete loss of radioactivity, confirming the observation that free ATP is unable to penetrate the cell membrane. These data, taken together with the fusion data, indicate that DOPC vesicles are being endocytosed, DOPC:DOPC-e vesicles are fusing, and free ATP does not enter cells. DOPC:POPA vesicles also could not be washed away, indicating that they also were fusing with cells and delivering the encapsulated contents into the cytoplasm.

Example 4

Endothelial Macromolecular Permeability.

Any use of the vesicles of this invention to deliver encapsulated molecules in vivo through the circulatory system in contrast to delivering molecules directly to cells requires that the vesicles and/or molecules must penetrate the vascular endothelium. The vascular endothelium constitutes a barrier, but the cell-to-cell barrier can be bridged, as for example, when leukocytes leave the circulation and enter the interstitial space. In order to address this issue, the effect of the lipid vesicles of this invention on endothelial permeability was measured.

HUVEC were grown to confluence on microporous filters (0.8 μm) in EGM. The cells were placed in a special chamber which allowed for the measurement of protein flux across the endothelial monolayer. The tracer used to examine the effects of the lipid vesicles on endothelial permeability was FITC-albumin (1 mg/ml). The FITC-albumin and the lipid vesicles were added to the endothelial cells at time zero. Every 5 minutes, a 500 μl sample of the supernatant was collected and then analyzed for fluorescence using the Perkin-Elmer LS 5OB Luminescence Spectrophotometer. DOPC vesicles had no effect on permeability, while HUVEC permeability increased in the presence of DOPC/DOPC-e, indicating that these vesicles created small gaps between adjacent endothelial cells.

Example 5

Metabolic Demand for ATP

As an example of determining the required optimum rate, the metabolic demand for ATP of rat liver cells was determined. Whole rat liver was isolated and placed in an isolation buffer (0.25 M sucrose, 0.04 M Tris at pH 7.2), minced with sterile scissors, and pieces of connective tissue were carefully trimmed. The liver was then passed through a #60 stainless steel wire mesh sieve, and the cellular effluent was collected on ice. The suspension was centrifuged at 4° C. for five minutes to pellet the cells. The supernatant was discarded, and the cells were re-suspended in oxygenation buffer (200 mM sucrose, 70 mM KCl, 5 mM maleate and 40 mM Tris, pH 7.3). Five milliliters of oxygenation buffer was placed in a Yellow Springs Instruments Oxygen Meter (Yellow Springs, Ohio) and allowed to equilibrate to 37° C. Fifty μl of the cell extract was placed in the chamber, achieving a 2–3 mg/ml final protein concentration. Baseline oxygen consumption was then monitored for 1 minute, after which 100 mM ADP was added to the cells, and State 2 respiration was measured. Next, 5 mM glutamate was added, and State 3 respiration was measured. The $ADP/O_2$ ratio was determined by measuring the amount of ADP added to the amount of oxygen consumed. Thus the State 3 respiration is a measure of how much ATP is consumed by the cells/minute/mg of tissue.

Example 6

ATP-SUV Accelerates Wound Healing

Superficial wounds (approximately 80 $mm^2$ circles) were inflicted to the integument on nude mice at the upper cranial area. ATP-SUV was then applied to the wound twice daily to provide the border cells of the wound with ATP. The ATP-SUV was placed directly over the wound in a specially designed applicator which kept the water-based ATP-SUV in direct contact with the wound.

Figure 2:
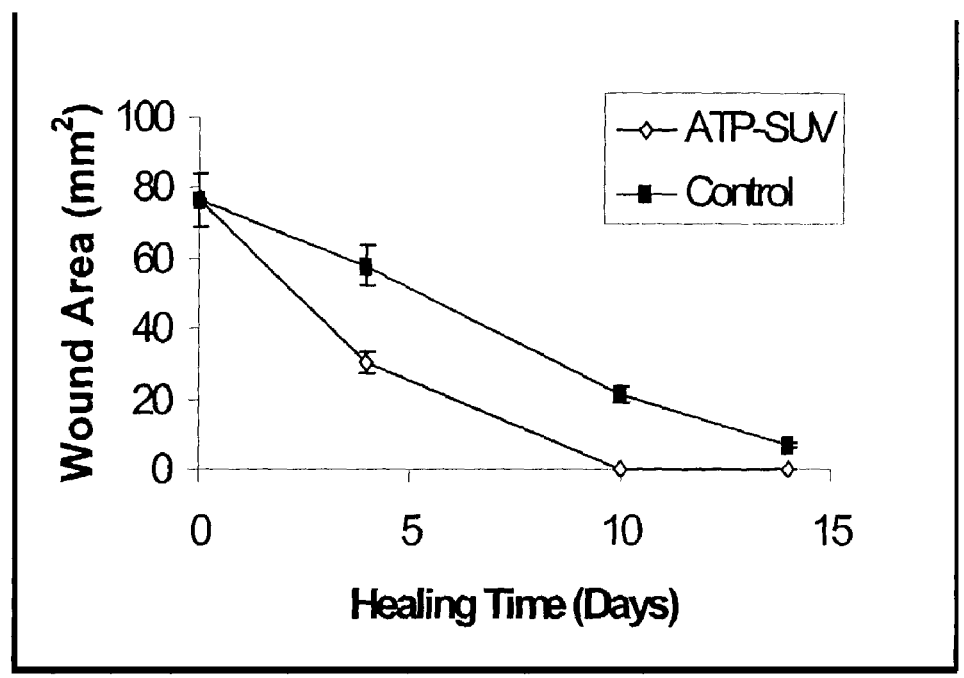
FIG. 2 shows the effects of the compositions of the invention on wound healing, in a nude mouse.

As seen in FIG. 2, wounds treated with ATP-SUV compared to those treated with control substances healed more quickly. The curve for ATP-SUV-treated wounds, plotting wound area against healing time, demonstrates a logarithmic curve, while controls showed a more linear rate of healing. On Day 4, a difference of approximately 30 mm² is observed between the ATP-SUV treatment ($\approx$30 mm²; less than half of the original wound area) and the control treatment ($\approx$60 mm²); while at day 10, the wound area is virtual gone in ATP-SUV treated wounds, but not in control treated wounds ($\approx$25 mm²). Qualitatively, Day 4 of VitalSol treated wounds resembled those of Day 10 in controls; while Day 10 mimicked the controls at Day 17. The wound was healed by Day 17 in wounds treated with ATP-SUV, while controls on this day were not yet completely healed.

Example 7

Limb Reattachment

Hind legs were amputated from rats, and the major feed arteries for the severed limbs were cannulated for infusion of ATP-SUV, loaded in a 1 mM ATP solution. The limbs were perfused with ATP-SUV or control solutions (see Table 1) every 3 hours, or as deemed necessary by the change in tissue ATP levels. The arterial pressure of the limbs were monitored during infusion to decrease the chance of flow-induced injury, and to monitor the overall preservation of the severed limbs (higher perfusion pressures may indicate limb morbidity). Following the preservation period, the limbs were flushed with Ringers to remove traces of ATP-SUV. The limbs were then surgically reattached, and external indices of limb function after anastomoses were evaluated (limb color, evidence of microthrombi, coagulation, limb temperature). The animals prior to and following replantation received heparin to prevent hemostasis. In addition, animals were placed on antibiotic therapy to reduce infection. Control limbs were perfused with vehicle only, vehicle and ATP only, or vehicle and SUVs only.

Figure 3:
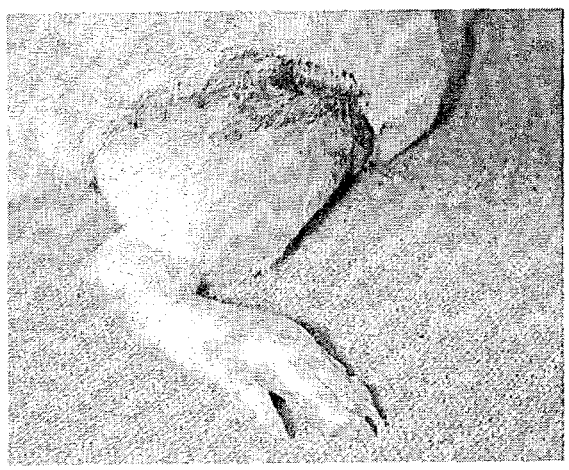
FIG. 3 shows the successful replantation of an amputated limb in a rat. The limb is fully functional after re-attachment.
Figure 3:
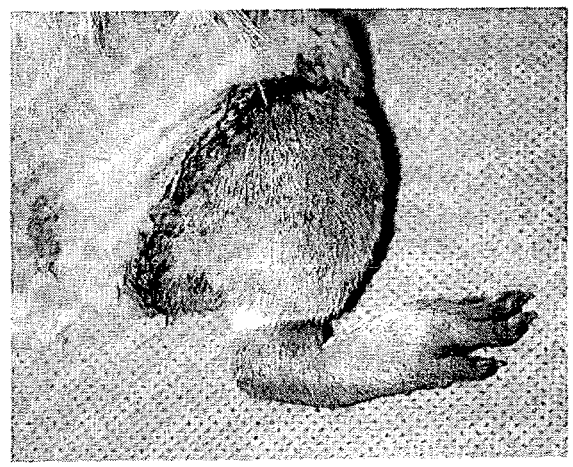

After 21 hours post-replantation, the ATP-SUV-treated limb exhibited a healthy pink color and had re-attained physiological temperature. After more than 150 days, those animals that received ATP-SUV-treated limbs were using these limbs as if the limb had never been amputated. The only qualitative side effect was a curling of the toes, most likely due to the lack of physical therapy, which most likely would have corrected this minor defect. In the controls, however, the limbs were darkly-colored and cold to the touch, exhibiting signs of necrosis. The summary of these results is shown in Table 1. Qualitative results are shown in FIG. 3.

TABLE 1

Summary of results from limb replantation studies

| Group | Limb outcome | n |
|---|---|---|
| Vehicle only | necrosis | 2 |
| Vehicle and 1 mM ATP only | necrosis | 2 |
| Vehicle and SUVs only | necrosis | 2 |
| Vehicle and ATP-SUV | survival | 5 |

Example 8

ATP-SUV Protects Isolated Hearts from Hypoxia

Hearts removed from rats were monitored using a Lagendorff heart perfusion apparatus. The hearts were cannulated and placed in a specially designed chamber, which perfused the heart, and allowed for the injection of ATP-SUV. The oxygenated perfusate, which was circulating to the heart was stopped, and ATP-SUV was injected into the heart. The heart was then placed in arrest by injecting a high potassium solution. The ATP-SUV was kept in the heart for 120 minutes at 37° C. under no-flow conditions. The heart was then flushed with oxygenated perfusate solution, and the performance of the heart was monitored. ATP-SUV treated hearts regained heart function compared to controls.

Example 9

Improvement in Blood Storage (Prophetic Example)

To ascertain whether ATP-containing vesicles preserve blood and whether the addition of the glycolytic intermediates phosphoenolpyruvate (PEP) and fructose-1,6-diphosphate (FDP) further improve viability, the following experiment is performed. Vesicles are constructed using DOPC only, following the methods of Example 2. Blood will be collected according to standard procedures into a bag containing a standard Dextrose-citrate-adenine-phosphate mixture (Baxter; Deerfield, Ill.). For each set of experiments, one unit of blood is divided into equal aliquots and is aseptically transferred to polyethylene bags containing no additional additives (control). Test substances will be added to the other aliquots as follows:

Control, no additives
Control, vesicles containing PEP, FDP and ribose
ATP-SUVs

At 30, 45, 60 and 90 days, aliquots are withdrawn, and the condition of the red blood cells is evaluated according to the following parameters: ATP content, hematocrit, hemoglobin, and cell viability (using Trypan blue (Sigma) exclusion or LIVE/DEAD kit (Molecular Products; Eugene, Oreg.). Anticipated results: cells stored in the presence of ATP containing vesicles will be in better condition than the controls; that is, ATP content will be higher, pH will have decreased less (indicating less glycolysis), and the red blood cells will have retained the biconcave shape typical of a functional red blood cell.

References

Alberts B, Johnson M A, Lewis J, Raff M, Roberts K, Walter P, (2002) Molecular Biology of the Cell. Garland Science, New York.

Ainscow, E. K., and Brand, M. D. (1999) Top-down control analysis of ATP turnover, glycolysis and oxidative phosphorylation in rat hepatocytes. Eur. J. Biochem. 263: 671–685.

Arakawa A, Ishiguro S, Ohki K, Tamai M. (1998) Preparation of liposome-encapsulating adenosine triphosphate. Tohoku J Exp Med 184: 39–47.

Brand, M. D. (1995). Measurement of mitochondrial proton motive force. In Bioenergetics, a Practical Approach/ Brown, G. C., and Cooper, C. E., eds. Oxford University Press, Oxford. 39–62.

Jahn R, Sudhof T C. (1999) Membrane fusion and exocytosis. Annu Rev Biochem 68: 863–911.

Puisieux F, Fattal E, Lahiani M, Auger J, Jouannet P, Couvreur P, Delattre J. (1994) Liposomes, an interesting tool to deliver a bioenergetic substrate (ATP). in vitro and in vivo studies. *J Drug Target* 2: 443–448.

Remington: the science and practice of pharmacy (2000) Alfonso R. Gennaro, chairman of the editorial board and editor. Edition: 20th ed. Lippincott Williams & Wilkins, Baltimore, Md.

What is claimed is:

1. A fusogenic vesicle, comprising:

ATP at a concentration of 1 mM to 50 mM, a phospholipid which is a stable vesicle former, wherein the phospholipid is a phosphatidylcholine, and at least one unstable vesicle forming member wherein the unstable vesicle forming member is PEG or a polar lipid having the structure of the formula (I) which is X-L-Z2, wherein X is H or a head group comprising a polar group selected from the group consisting of formulas (III), (IV), (V), (VI), and (VII)

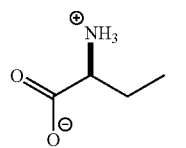 (III)

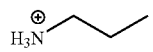 (IV)

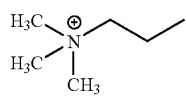 (V)

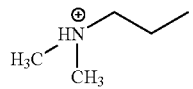 (VI)

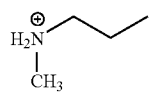 (VII)

L is an alkyl, and each Z is independently H, E, or the structure of formula (XI),

 (XI)

wherein E is an alkyl or alkenyl, and when one Z is H, the other Z is not H, and wherein the vesicle has a ratio of the stable vesicle former to the unstable vesicle forming member of 1:1 to 500:1 and a fusion rate of at least 20 vesicle fusions/second.

2. The vesicle of claim 1, wherein the fusion rate is at least $10^3$ vesicle fusions/second.

3. A method of delivering ATP to a cell, comprising contacting the cell with the vesicle of claim 1.

4. A method of delivering ATP to a cell, comprising contacting the cell with the vesicle of claim 2.

5. A method for treating a wound, comprising contacting the wound with a composition comprising the vesicle of claim 1.

6. A method for treating a wound, comprising contacting the wound with a composition comprising the vesicle of claim 2.

7. The method of claim 5, wherein the composition further comprises becaplermin.

8. The vesicle of claim 1, wherein the fusion rate is at least $10^6$ vesicle fusions/second.

9. The vesicle of claim 1, wherein the at least one unstable vesicle forming member is PEG.

10. The method of claim 3, wherein an amount of ATP delivered to the cell is sufficient to meet metabolic demand of the cell.

11. The method of claim 4, wherein an amount of ATP delivered to the cell is sufficient to meet metabolic demand of the cell.

12. A method of preserving tissue, comprising contacting tissue with the vesicle of claim 1.

13. A method of preserving tissue, comprising contacting tissue with the vesicle of claim 2.

14. A method of improving the productivity of a bioreactor having at least one cell, comprising contacting the cell with the vesicle of claim 1.

15. A method of improving the productivity of a bioreactor having at least one cell, comprising contacting the cell with the vesicle of claim 2.

16. A vesicle, comprising

ATP, at a concentration of 1 mM to 50 mM

DOPC, and POPA wherein a ratio of DOPC:POPA is 1:1 to 500:1.

17. The vesicle of claim 16, wherein a ratio of DOPC:POPA is 10:1 to 100:1.

* * * * *